(12) United States Patent
Sander et al.

(10) Patent No.: US 7,829,680 B1
(45) Date of Patent: Nov. 9, 2010

(54) SYSTEM AND METHOD FOR ISOLATION OF GLUTEN AS A CO-PRODUCT OF ETHANOL PRODUCTION

(75) Inventors: Rob Sander, Columbus, NE (US); Larry D. Fritz, Columbus, NE (US)

(73) Assignee: ProGold Plus, Inc., Columbus, NE (US)

( * ) Notice: Subject to any disclaimer, the term of this patent is extended or adjusted under 35 U.S.C. 154(b) by 426 days.

(21) Appl. No.: 11/894,155

(22) Filed: Aug. 20, 2007

Related U.S. Application Data (60) Provisional application No. 60/838,667, filed on Aug. 18, 2006.

(51) Int. Cl.
*A23J 1/00* (2006.01)
*C07K 1/00* (2006.01)

(52) U.S. Cl. ............... 530/412; 530/413; 530/350; 530/300

(58) Field of Classification Search ............ None
See application file for complete search history.

*Primary Examiner*—Hope A Robinson
(74) *Attorney, Agent, or Firm*—Suiter Swantz pc llo (57) ABSTRACT

The present invention is a method for protein isolation as a co-product of alcohol production. The method includes receiving grain product at a holding receptacle, the grain product being at least one of whole stillage, dried distillers grain, and wet distillers grain. The method further includes directing the grain product from the holding receptacle over a plurality of screens, thereby allowing a fiber-containing portion of the grain product to be collected on the plurality of screens and further allowing a protein-containing portion of the grain product and an oil-containing portion of the grain product to pass through the plurality of screens. The method further includes directing the protein-containing portion and the oil-containing portion over a finishing screen, thereby allowing remaining fiber fractions from the protein-containing portion and the oil-containing portion to be collected on the finishing screen and further allowing the protein-containing portion and the oil-containing portion to pass through the finishing screen. Further, the method includes centrifuging the protein-containing portion and the oil-containing portion for isolating a protein fraction, an oil fraction, and a water and minerals fraction.

16 Claims, 6 Drawing Sheets

SYSTEM AND METHOD FOR ISOLATION OF GLUTEN AS A CO-PRODUCT OF ETHANOL PRODUCTION

CROSS-REFERENCE TO RELATED APPLICATIONS

The present application claims priority under 35 U.S.C. §119(e) to U.S. Provisional Application No. 60/838,667 entitled: System and Method for Isolation of Gluten as a Co-Product of Ethanol Production filed Aug. 18, 2006, which is hereby incorporated by reference in its entirety.

FIELD OF THE INVENTION

The present invention generally relates to the field of ethanol production, and more particularly to a system and method for isolation of gluten as a co-product of ethanol production.

BACKGROUND OF THE INVENTION

Manufacturers use two major processes to produce alcohol or other starch-based products. These two processes, dry milling (mash distillation) and wet milling are very different, as are their co-products. The primary co-products from dry milling are distillers' grains, while the primary co-products from wet milling are gluten products. Co-products from the dry milling and/or wet milling of corn have important nutritional properties that add value to feeding rations and livestock programs. However, current systems and methods of isolating co-products from dry milling and wet milling processes may require unnecessary steps and equipment, which may be time-consuming and costly. Further, current systems and methods for isolating co-products may not efficiently utilize the various co-products.

Accordingly, it would be desirable to provide a system and method for isolating gluten as a co-product of ethanol production which addresses the above-referenced shortcomings of current solutions.

SUMMARY OF THE INVENTION

Accordingly, an embodiment of the present invention is directed to a method for protein isolation as a co-product of alcohol production, including: receiving a grain product at a holding receptacle, the grain product being at least one of whole stillage, dried distillers grain and wet distillers grain; directing the grain product from the holding receptacle over a plurality of screens, thereby allowing a fiber-containing portion of the grain product to be collected on the plurality of screens and further allowing a protein-containing portion of the grain product and an oil-containing portion of the grain product to pass through the plurality of screens; directing the protein-containing portion and the oil-containing portion over a finishing screen, thereby allowing remaining fiber fractions from the protein-containing portion and the oil-containing portion to be collected on the finishing screen and further allowing the protein-containing portion and the oil-containing portion to pass through the finishing screen and centrifuging the protein-containing portion and the oil-containing portion for isolating a protein fraction, an oil fraction, and a water and minerals fraction.

An additional embodiment is directed to a system for protein isolation as a co-product of alcohol production, including: a holding receptacle configured for receiving grain product, the grain product being at least one of whole stillage, dried distillers grain and wet distillers grain; a screen system, the screen system including a plurality of screens, the screen system being configured for receiving the grain product from the holding receptacle, each of the plurality of screens configured for retaining a fiber-containing portion of the grain product and further configured for allowing flow-through of a protein-containing portion of the grain product and an oil-containing portion of the grain product; a transfer receptacle, the transfer receptacle being configured for receiving the protein-containing portion of the grain product and the oil-containing portion of the grain product from the screen system; a finishing screen, the finishing screen being configured for receiving the protein-containing portion and the oil-retaining portion from the transfer receptacle, the finishing screen further being configured for retaining remaining fiber fractions of the protein-containing portion and the oil-containing portion, the finishing screen further being configured for allowing flow-through of the protein-containing portion and the oil-containing portion; and a centrifuge assembly, the centrifuge assembly being configured for receiving the protein-containing portion and the oil-retaining portion which pass through the finishing screen, the centrifuge assembly being further configured for centrifuging the protein-containing portion and the oil-containing portion for isolating a protein fraction, an oil fraction, and a water and minerals fraction.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous objects and advantages of the present invention may be better understood by those skilled in the art by reference to the accompanying figures in which.

DESCRIPTION OF THE INVENTION

Reference will now be made in detail to the presently preferred embodiments of the invention, examples of which are illustrated in the accompanying drawings.

Figure 1:
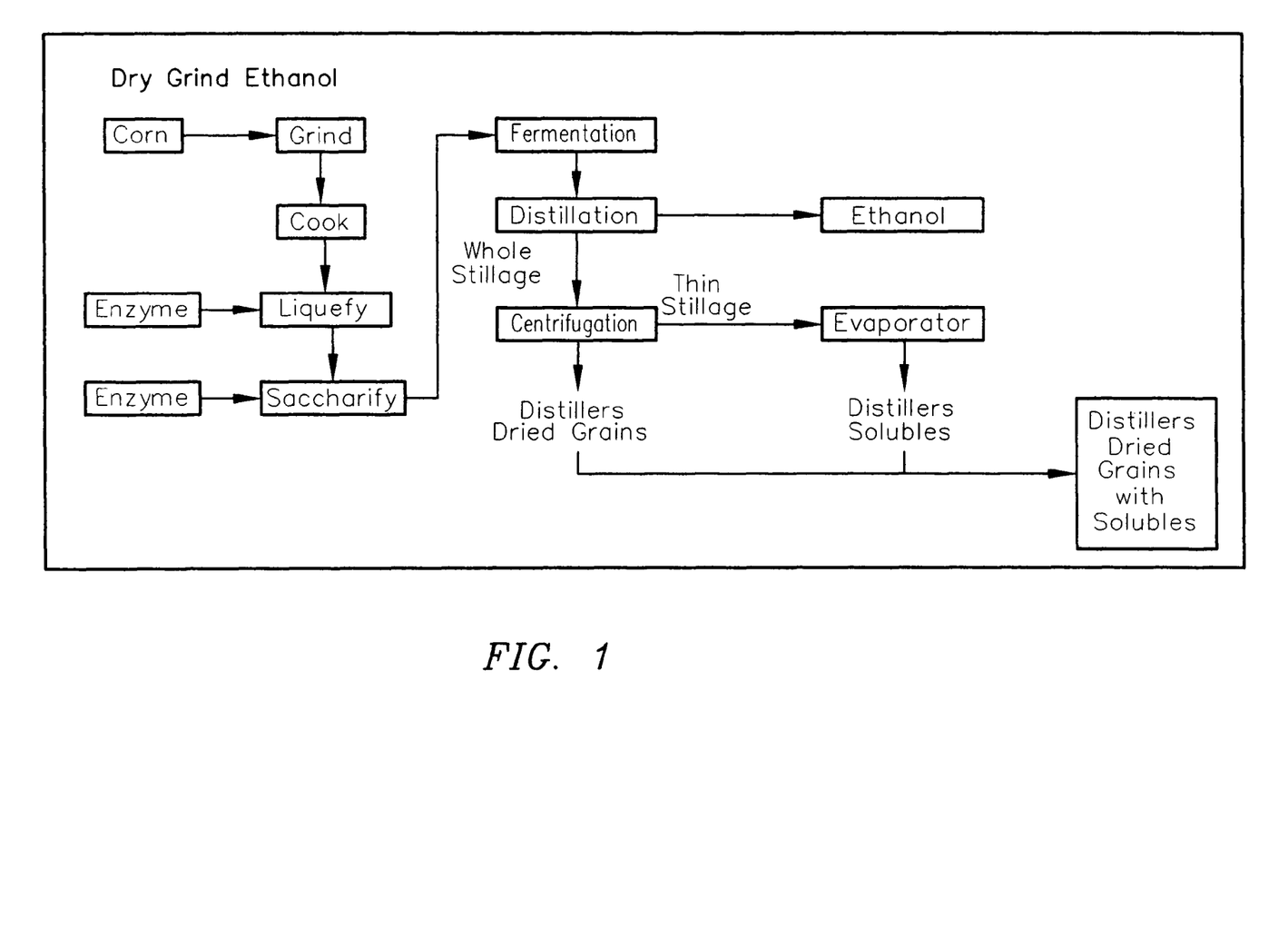
FIGS. 1 and 3 are block diagram illustrations of exemplary systems for dry milling of corn.
Figure 3:
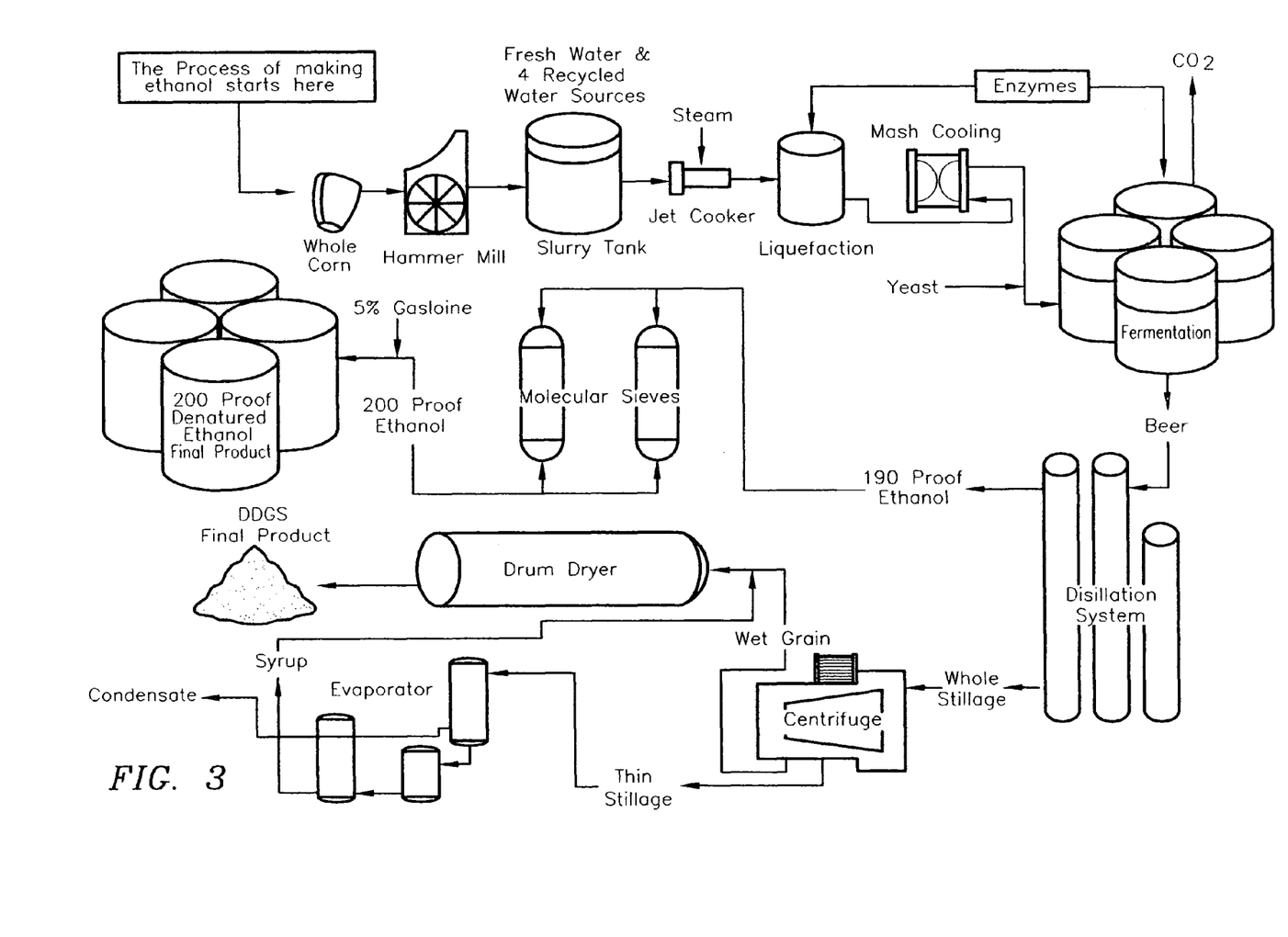

Referring generally to FIGS. 1 and 3, exemplary systems for dry milling of grain, such as corn, are shown. Typical dry milling systems, as shown, may produce ethanol via the following steps: corn is ground into coarse flour; the coarse flour is combined with water and/or enzymes are added to convert starch to sugar (thus forming the "mash"); the mash is cooked and sterilized; the mash is cooled; yeast and malt enzymes are added to the mash to allow the sugar to convert to ethanol and carbon dioxide (via fermentation); the mash is sent to distillation where ethanol is extracted leaving "spent mash" or whole stillage; the whole stillage goes to either screen/press or centrifuge (ex-decanting centrifuge) to separate out as much liquid as possible (the liquid being distillers solubles or "thin stillage"); the thin stillage may then go back into the system (i.e., be recycled), be sold as livestock feed, or be made into a syrup known as condensed distillers solubles (CDS); and the remaining part of the whole stillage (the wet grain/wet distillers grain) may be sold as livestock feed, dried into dried distillers grain (DDG), such as via a drum dryer, or dried into DDG to which syrup (CDS) may be added to produce distillers dried grains w/solubles (DDGS).

Figure 2:
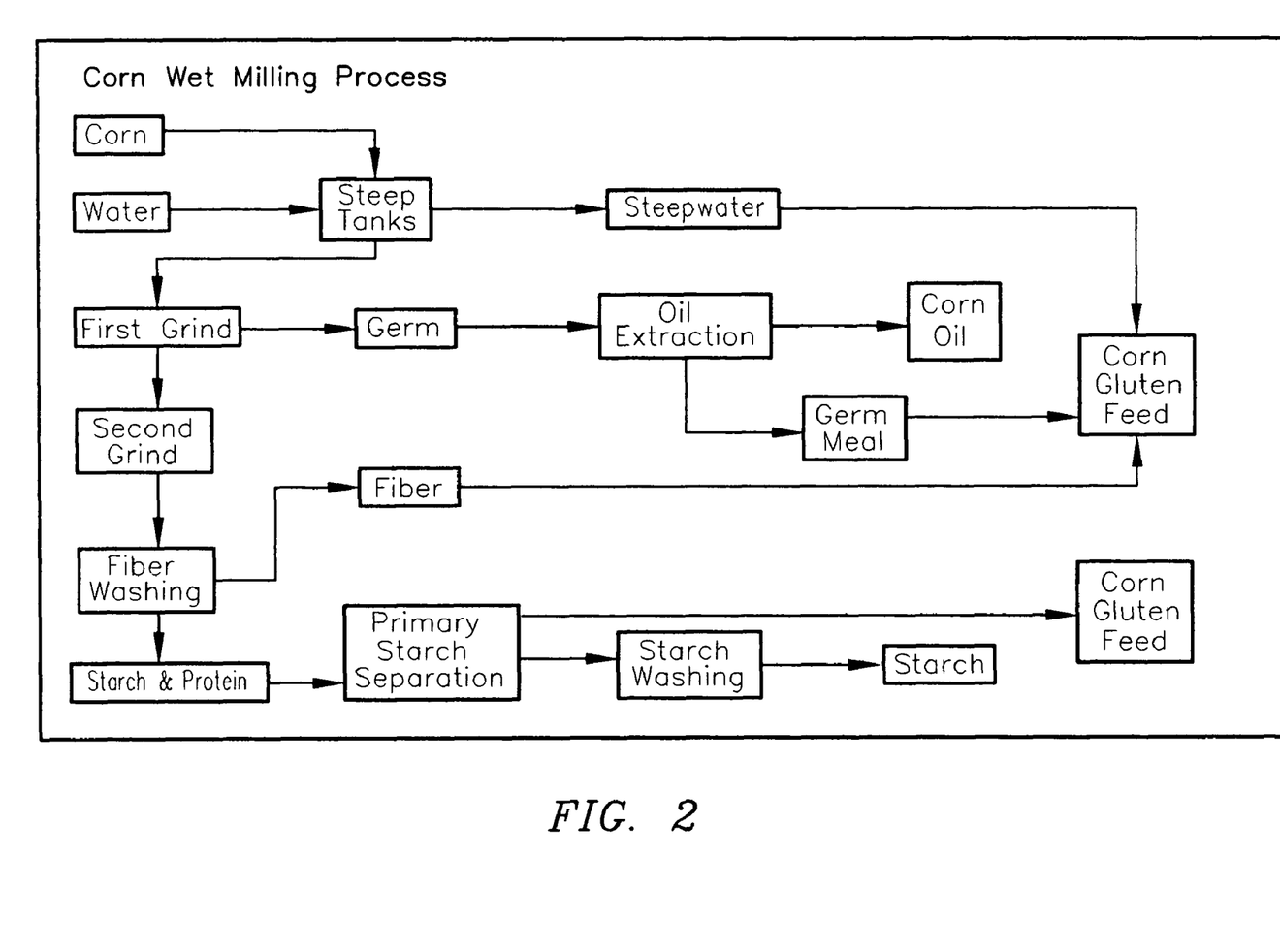
FIG. 2 is a block diagram illustration of an exemplary system for wet milling of corn.

Referring generally to FIG. 2, an exemplary system for wet milling of corn is shown. A typical wet milling system produces alcohol or other starch-based products via the following steps: corn is soaked in a steep tank w/sulfur dioxide treated water to separate the starch and insoluble protein; the corn is removed and coarse milled ($1^{st}$ grind) to separate out the germ, wherein oil may be extracted from the germ and refined into corn oil, while the germ may be dried to form corn germ meal; the corn (w/o germ) is pulverized ($2^{nd}$ grind), washed and screened to separate the fiber (bran) from the starch and gluten/protein; the corn (w/o germ and fiber) is then centrifuged to separate the starch from the gluten/protein; the gluten/protein (60% protein) is concentrated, filtered and dried to produce corn gluten meal; the starch is separated again to reduce protein content to 0.3%, thereby producing purified starch, which may be used to make ethanol and corn sweeteners.

Figure 4A:
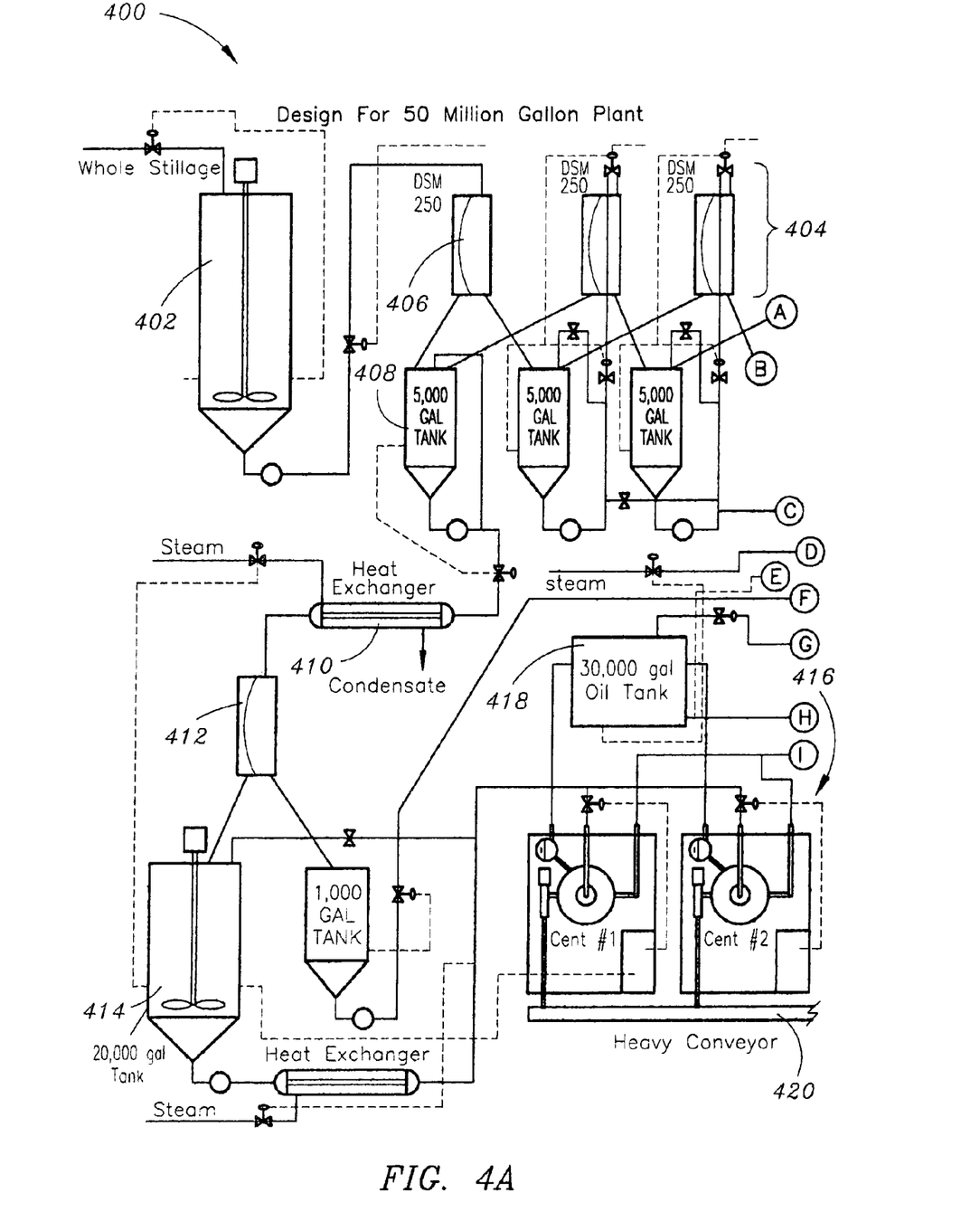
FIGS. 4A and 4B are block diagram illustrations of a system for isolation of gluten as a co-product of ethanol production in accordance with an exemplary embodiment of the present invention.
Figure 4B:
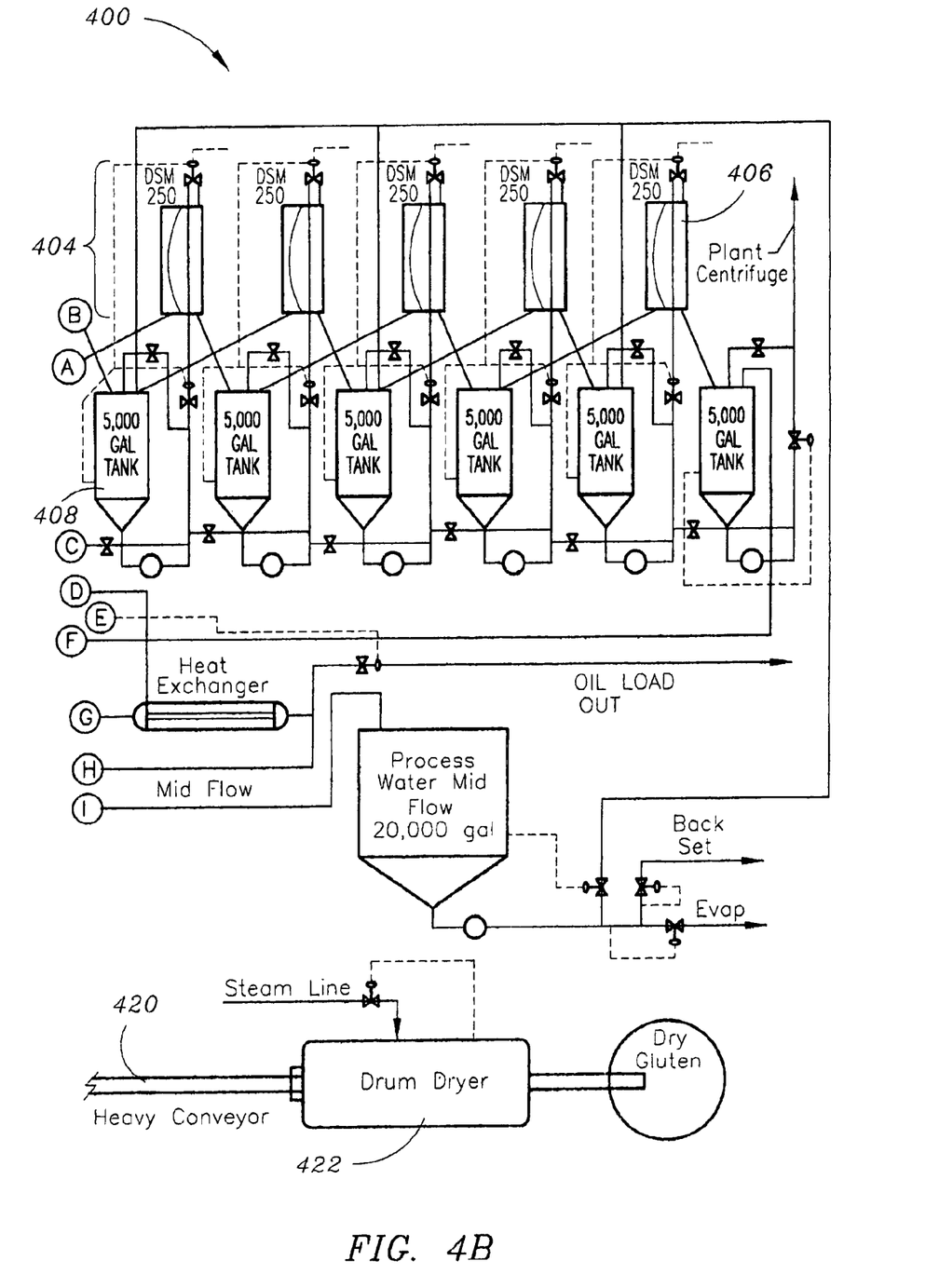

Referring generally to FIGS. 4A and 4B, a system for protein (ex-gluten) isolation as a co-product of alcohol (ex-ethanol) production in accordance with an exemplary embodiment of the present invention is shown. In a present embodiment, the system 400 may include a holding receptacle 402, such as a 40,000 gallon tank, which may be configured for receiving a grain product. In an exemplary embodiment, the grain product may be whole stillage, such as the post-distillation product (ex-spent mash) described above. In further embodiments, the grain product may be dried distillers grain (DDG) as described above. In still further embodiments, the grain product may be wet grain/wet distillers grain (which may be sixty (60) percent moisture) as described above. For example, the grain product may be received from an ethanol plant and may be a product/co-product that remains after completion of the distillation stage in a dry milling system as shown in FIGS. 1 and 3 (i.e., mash minus ethanol). In an exemplary embodiment, the grain product is directed from the holding receptacle 402 to a screen system 404. The screen system 404 may include a plurality or series of screens, such as gravity-fed or DSM® screens 406, and may be configured for receiving the grain product from the holding receptacle 402. For instance, the screen system 404 may include eight DSM® screens 406, each screen 406 being a two hundred and fifty (250) micron screen. In additional embodiments the screen may be any size included in the range of one hundred fifty (150) microns through two hundred fifty (250) microns. In further embodiments, each screen 406 may be a one hundred and eighty degree screen.

In exemplary embodiments, the grain product may be pumped over the series of screens 406, with each of the plurality of screens 406 configured for retaining a fiber-containing portion of the grain product (i.e., the overflow or portion which passes over the screens 406). Further, each of the plurality of screens 406 is configured for allowing flow-through of a protein-containing portion of the grain product (i.e., the underflow) and an oil-containing portion of the grain product (i.e., the underflow). For example, approximately eighty percent (80%) of total available oil of the grain product may pass through the screens as underflow. The flow-through (ex- the oil-containing portion and the protein-containing portion) at each screen 406 may be captured by a series of transfer receptacles 408, from which, the flow-through may be directed/pumped over the next screen 406 of the screen system 404. For instance, the transfer receptacles may be a series of five thousand (5,000) gallon tanks. In current embodiments of the present invention, process water may be added to the overflow (ex- the fiber-containing portion) for hydrating the fiber overflow as may be necessary for facilitating pumping of the grain product (ex-fiber-containing portion) over the screens 406. This may be advantageous in that no fresh water may need to be added.

In additional embodiments, the grain product may be fed to/pumped to/pumped over the screens 406 at a header pressure of at least eighty (80) pounds per square inch (psi). Preferably, the grain product may be fed to/pumped to/pumped over the screens 406 at a header pressure of between one hundred (100) psi and one hundred and twenty (120) psi. Further, as the grain product is pumped through/over the series of screens, it may be maintained at a temperature of at least or approximately one hundred eighty (180) degrees Fahrenheit. In current embodiments of the present invention, one or more heat exchangers 410 may be included/connected in-line for promoting maintenance of the temperature of the grain product at the desired temperature (ex-one hundred eighty (180) degrees Fahrenheit). Also, as the grain product is pumped over/through the series of screens 406, a continuous flow counter current may be created meaning that the flow-through (ex-protein containing portion and oil-containing portion) moves backward (ex- to a preceding transfer receptacle 408), while the overflow (ex-fiber-containing portion) moves forward (to a next screen 406) (as shown in FIGS. 4A and 4B).

In exemplary embodiments, once the grain product and/or fiber-containing portion/overflow has been pumped over all of the screens 406 of the screen system 404, the fiber-containing portion which had been collected on and pumped over the screens 406 may be directed to/pumped back to the ethanol plant. For example, once at the ethanol plant, the fiber-containing portion may be: a.) placed in a decanting centrifuge, dried and sold as feed stock; or b.) sold as wet feed. The feed value of the fiber-containing portion/overflow/feed stock/feed product may be approximately 20% protein, 15% fiber and 5% fat.

In further embodiments, the system 400 includes a finishing screen 412. The finishing screen 412 may be configured for receiving the protein-containing portion and the oil-containing portion from one of the transfer receptacles 408. Further, the finishing screen 412 may be a gravity-fed or DSM® screen. In exemplary embodiments, the finishing screen 412 is further configured for retaining remaining fiber fractions of the protein-containing portion and the oil-containing portion which were not retained/captured by the screens 406 of the screen system 404. The finishing screen 412 is also configured for allowing flow-through of the protein-containing portion of the grain product and the oil-containing portion of the grain product. For promoting its fiber fraction retention functionality, the finishing screen 412 may have a smaller slot width than the screens 406 of the screen system 404. For example, the finishing screen 412 may be a one hundred and fifty (150) micron screen, but may also be any size included in the range of one hundred (100) microns through one hundred fifty (150) microns. In additional embodiments, the finishing screen 412 may be a one hundred and eighty (180) degree screen. Further, one or more of the heat exchangers 410 may be included/connected in-line for promoting maintenance of the temperature of the protein-containing portion and/or the oil-containing portion at the desired temperature (ex-one hundred eighty (180) degrees Fahrenheit). The protein-containing portion and the oil-containing portion, which flow-through the finishing screen, may be received in a receiving vessel or tank 414.

In additional embodiments, the system 400 includes a centrifuge assembly 416. The centrifuge assembly 416 may be a 3-stage centrifuge assembly configured for receiving the protein-containing portion and the oil-containing portion which pass through the finishing screen 412. In exemplary embodiments, the protein-containing portion and the oil-containing portion may be directed or pumped from the receiving vessel/tank 414 to the centrifuge assembly 416. The centrifuge assembly 416 may be further configured for centrifuging the protein-containing portion and the oil-containing portion for isolating a protein fraction, an oil fraction and a water and minerals fraction. In current embodiments of the present invention, the isolated oil fraction may pass from/exit the centrifuge assembly 416 as centrifuge overflow, may be the lightest fraction, and may be ninety-nine percent (99%) pure oil, such as 99% pure corn oil (ex-99% solids), which may be sent to a storage tank 418 for shipping.

In exemplary embodiments, the isolated water and minerals fraction (which may also include small amounts of soluble protein) may pass from/exit the centrifuge assembly 416 as centrifuge mid-flow. Further, the water and minerals fraction may be directed/pumped to the ethanol plant where it may be used as backset, used to hydrate new grain/corn before processing and/or evaporated via an evaporator of the ethanol plant. Still further, the water and minerals fraction may be recycled/pumped back through the system 400 and used as process water, which may be used to hydrate the fiber overflow as discussed above.

In further embodiments of the present invention, the isolated protein fraction may pass from/exit the centrifuge assembly 416 as centrifuge underflow. For example, the protein fraction may be approximately 75% moisture, approximately 50-55% protein, approximately 20% dry solids, approximately 5% fiber, and approximately 3% fat. Because free oil, water and minerals have been removed from the protein fraction via centrifugation, the protein fraction may be a "purified" protein stream, such as a "purified" gluten stream. In additional embodiments, the system 400 may include a conveyer 420, such as a heavy conveyer, for transporting the protein fraction from the centrifuge assembly 416 to a dryer 422. For instance, the dryer 422 may be a gluten rotary drum dryer. In exemplary embodiments, the dryer 422 may be configured for drying/removing moisture from the isolated protein fraction. For example, the isolated protein fraction may be dried to approximately 10% moisture and stockpiled for shipping as a high feed value product.

Figure 5:
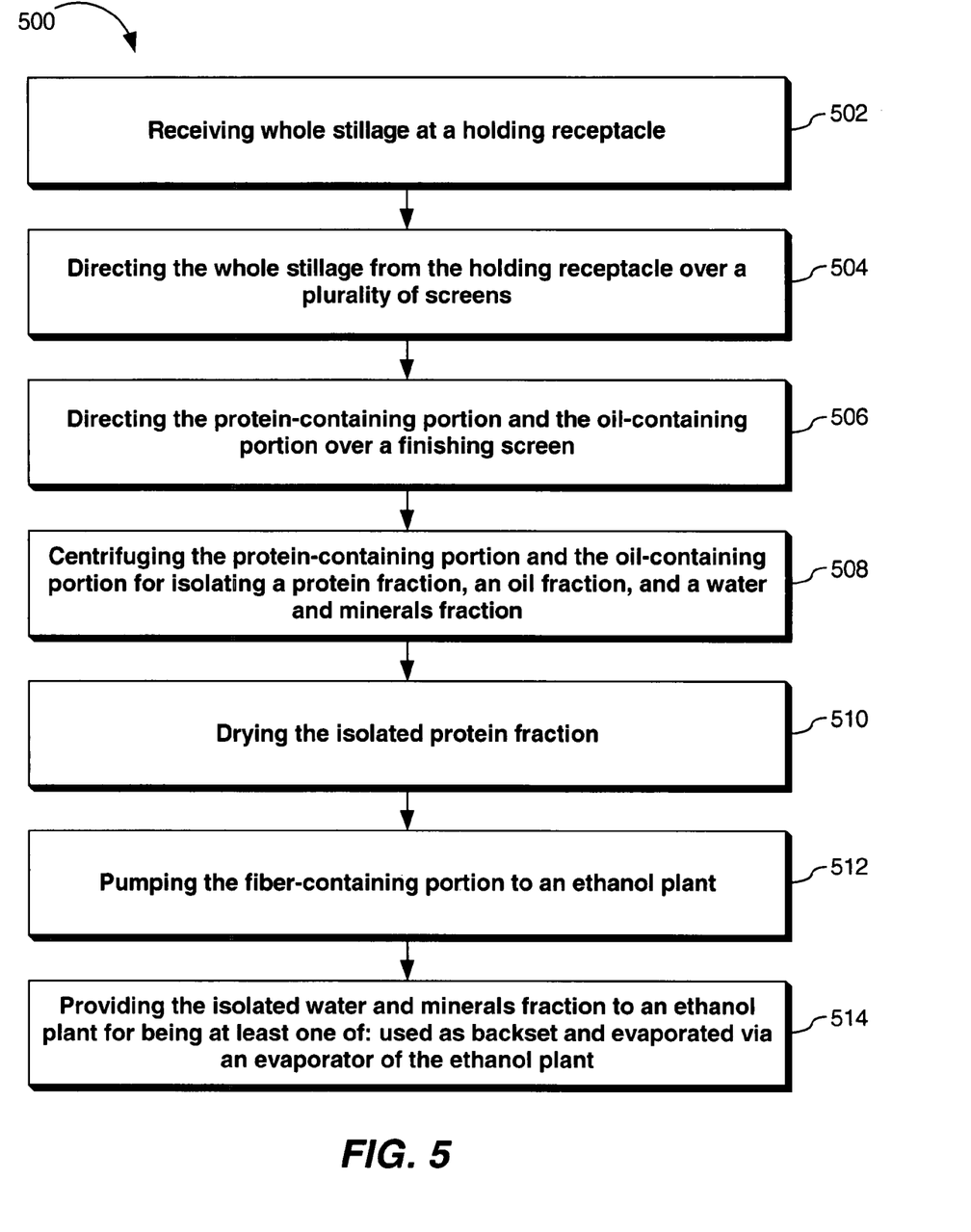
FIG. 5 is a flowchart illustrating a method for protein isolation as a co-product of alcohol production.

Referring generally to FIG. 5, a flowchart illustrating a method for protein isolation as a co-product of alcohol production is shown. In an exemplary embodiment, the method 500 includes receiving grain product at a holding receptacle 502. The method 500 may further include directing the grain product from the holding receptacle over a plurality of screens 504, thereby allowing a fiber-containing portion of the grain product to be collected on the plurality of screens and further allowing a protein-containing portion of the grain product and an oil-containing portion of the grain product to pass through the plurality of screens. In exemplary embodiments, the fiber-containing portion includes between 10-30% protein, between 5-25% fiber and between 1-10% fat. The method 500 may further include directing the protein-containing portion and the oil-containing portion over a finishing screen 506, thereby allowing remaining fiber fractions from the protein-containing portion and the oil-containing portion to be collected on the finishing screen and further allowing the protein-containing portion and the oil-containing portion to pass through the finishing screen. The method 500 may further include centrifuging the protein-containing portion and the oil-containing portion for isolating a protein fraction, an oil fraction, and a water and minerals fraction 508. In current embodiments of the present invention, the isolated oil fraction includes at least ninety-nine percent (99%) pure corn oil. In exemplary embodiments, the isolated protein fraction may include between thirty percent (30%) and sixty-five percent (65%) protein. In further embodiments, the isolated protein fraction may include between ten percent (10%) and thirty percent (30%) dry solids. In still further embodiments, the isolated protein fraction may include between seventy percent (70%) and ninety percent (90%) moisture.

In additional embodiments, the method 500 may further include drying the isolated protein fraction 510. In exemplary embodiments, the dried isolated protein fraction includes between five percent (5%) and fifteen percent (15%) moisture. The method 500 may further include pumping the fiber-containing portion to an ethanol plant 512. The method 500 may further include providing the isolated water and minerals fraction to an ethanol plant for being at least one of: used as backset and evaporated via an evaporator of the ethanol plant 514.

In further embodiments, the method 500 may include adding process water for hydrating the fiber-containing portion collected on the plurality of screens 516. In exemplary embodiments, at least one of the grain product, the protein-containing portion and the oil-containing portion is maintained at a temperature of at least one hundred eighty (180) degrees Fahrenheit. In additional embodiments, the step of directing the grain product over the plurality of screens 504 and/or the step of directing the protein-containing portion and the oil-containing portion over a finishing screen 506 includes pumping the grain product to the plurality of screens at a header pressure of at least eighty (80) pounds per square inch (psi), but preferably between one hundred (100) pounds per square inch (psi) and one hundred twenty (120) pounds per square inch (psi).

It is noted that in embodiments in which the grain product is wet distillers grain or dried distillers grain, water may need to be added during the process to facilitate pumping of the wet distillers grain or dried distillers grain through the system 400.

It is believed that the system and method for isolation of gluten as a co-product of ethanol production of the present invention and many of its attendant advantages will be understood by the forgoing description. It is also believed that it will be apparent that various changes may be made in the form, construction and arrangement of the components and steps thereof without departing from the scope and spirit of the invention or without sacrificing all of its material advantages. The form herein before described being merely an explanatory embodiment thereof.

What is claimed is:

1. A method for protein isolation as a co-product of alcohol production, comprising:
receiving a grain product at a holding receptacle, the grain product being at least one of whole stillage, dried distillers grain and wet distillers grain;
directing the grain product from the holding receptacle over a plurality of screens, thereby allowing a fiber-containing portion of the grain product to be collected on the plurality of screens and further allowing a protein-containing portion of the grain product and an oil-containing portion of the grain product to pass through the plurality of screens;

directing the protein-containing portion and the oil-containing portion over a finishing screen, thereby allowing remaining fiber fractions from the protein-containing portion and the oil-containing portion to be collected on the finishing screen and further allowing the protein-containing portion and the oil-containing portion to pass through the finishing screen;

centrifuging the protein-containing portion and the oil-containing portion to isolate a protein fraction, an oil fraction, and a water and minerals fraction; and recovering the isolated protein fraction.

2. The method as claimed in claim 1, further comprising: drying the isolated protein fraction.

3. The method as claimed in claim 1, wherein the isolated oil fraction includes at least ninety-nine percent (99%) pure corn oil.

4. The method as claimed in claim 1, wherein the isolated protein fraction includes between thirty percent (30%) and sixty-five percent (65%) protein.

5. The method as claimed in claim 1, wherein the isolated protein fraction includes between ten percent (10%) and thirty percent (30%) dry solids.

6. The method as claimed in claim 1, wherein the isolated protein fraction includes between seventy percent (70%) and ninety percent (90%) moisture.

7. The method as claimed in claim 1, wherein the fiber-containing portion includes between 10-30% protein, between 5-25% fiber and between 1-10% fat.

8. The method as claimed in claim 2, wherein the dried isolated protein fraction includes between five percent (5%) and fifteen percent (15%) moisture.

9. The method as claimed in claim 1, wherein the step of directing the grain product over the plurality of screens includes pumping the grain product to the plurality of screens at a header pressure of at least one hundred (100) pounds per square inch (psi).

10. The method as claimed in claim 1, wherein at least one of the grain product, the protein-containing portion and the oil-containing portion is maintained at a temperature of at least one hundred eighty (180) degrees Fahrenheit.

11. A system for protein isolation as a co-product of alcohol production, comprising:

a holding receptacle configured for receiving a grain product, the grain product being at least one of whole stillage, dried distillers grain, and wet distillers grain;

a screen system, the screen system including a plurality of screens, the screen system being configured for receiving the grain product from the holding receptacle, each of the plurality of screens configured for retaining a fiber-containing portion of the grain product and further configured for allowing flow-through of a protein-containing portion of the grain product and an oil-containing portion of the grain product;

a transfer receptacle, the transfer receptacle being configured for receiving the protein-containing portion of the grain product and the oil-containing portion of the grain product from the screen system;

a finishing screen, the finishing screen being configured for receiving the protein-containing portion and the oil-retaining portion from the transfer receptacle, the finishing screen further being configured for retaining remaining fiber fractions of the protein-containing portion and the oil-containing portion, the finishing screen further being configured for allowing flow-through of the protein-containing portion and the oil-containing portion; and a centrifuge assembly, the centrifuge assembly being configured for receiving the protein-containing portion and the oil-retaining portion which pass through the finishing screen, the centrifuge assembly being further configured for centrifuging the protein-containing portion and the oil-containing portion to isolate a protein fraction, an oil fraction, and a water and minerals fraction.

12. The system as claimed in claim 11, further comprising:

a drum dryer, the drum dryer being configured for receiving the isolated protein fraction from the centrifuge assembly, the drum dryer being further configured for drying the isolated protein fraction.

13. The system as claimed in claim 11, wherein the finishing screen and the plurality of screens of the screen system are gravity-fed screens.

14. The system as claimed in claim 11, further comprising:

an inline heat exchanger configured for maintaining a temperature of at least one of the grain product, the protein-containing portion and the oil-containing portion.

15. The system as claimed in claim 11, wherein each of the plurality of screens of the screen system are 250 micron screens.

16. The system as claimed in claim 11, wherein the finishing screen is a 150 micron screen.

* * * * *